(12) United States Patent
Mueller-Westerhoff et al.

(10) Patent No.: US 6,933,399 B2
(45) Date of Patent: Aug. 23, 2005

(54) FUNCTIONALIZED METAL COMPLEXES

(75) Inventors: Ulrich T. Mueller-Westerhoff, Storrs, CT (US); Richard W. Sanders, Lisbon, CT (US)

(73) Assignee: The University of Connecticut, Storrs, CT (US)

(*) Notice: Subject to any disclaimer, the term of this patent is extended or adjusted under 35 U.S.C. 154(b) by 165 days.

(21) Appl. No.: 10/429,206

(22) Filed: May 2, 2003

(65) Prior Publication Data

US 2003/0225296 A1 Dec. 4, 2003

Related U.S. Application Data

(60) Provisional application No. 60/378,179, filed on May 2, 2002.

(51) Int. Cl.$^7$ ............................ C07F 17/02; C07F 19/00; C07F 15/00
(52) U.S. Cl. ........................... 556/28; 556/136; 556/146
(58) Field of Search ........................... 556/28, 136, 146

(56) References Cited

U.S. PATENT DOCUMENTS

| | | | |
|---|---|---|---|
| 3,743,964 A | | 7/1973 | Drexhage et al. .......... 331/94.5 |
| 3,806,462 A | * | 4/1974 | Bloom ........................ 252/587 |
| 3,875,199 A | * | 4/1975 | Bloom ........................ 556/136 |
| 4,593,113 A | * | 6/1986 | Kauffman ................... 556/136 |
| 4,806,664 A | * | 2/1989 | Schrott et al. .............. 556/136 |
| 6,051,207 A | | 4/2000 | Klaveness et al. ........... 424/9.1 |
| 6,264,914 B1 | | 7/2001 | Klaveness et al. .......... 424/1.65 |

OTHER PUBLICATIONS

Crowley, J.I. et al. "Polymeric Films as Materials for Ablation-Type Holeburning with IR Lasers." IBM Technical Disclosure Bulletin. Apr., 1982. vol. 24, No. 11B, p. 6186.
Drexhage, K.H. and Muller-Westerhoff, U.T. "New Q-Switch Compounds for Infrared Lasers," IEEE Journal of Quantum Electronics. Sep., 1972. vol. QE-8, No. 9, p. 759.
Grimaldi, John J. and Lehn, Jean-Marie. "Multicarrier Transport: Coupled Transport of Electrons and Metal Cations Mediated by an Electron Carrier and a Selective Cation Carrier." Journal of the American Chemical Society. Feb. 28, 1979. pp. 1333-1334.
Herman, Zelek S. et al. Electronic Spectra and Structure of Bis(ethylene-1,2-dithiolato)nickel and Bis(propene-3-thione-1-thiolato)nickel. Inorganic Chemistry. 1982. vol. 21, No. 1, pp. 46-56.
Mueller-Westerhoff, Ulrich T. and Alscher, Arnold. "Transition-Metal Complexes of Malonaldehyde and Dithiomalonaldehyde." Angew. Chemical International Edition English. 1980. vol. 19, No. 8, pp. 639-639.

Mueller-Westerhoff, Ulrich T. and Vance, Blake. "Dithiolenes and Related Species." Comprehensive Coordination Chemistry: The Synthesis, Reactions, Properties & Applications of Coordination Compounds. 1987. Pergamon Press. pp. 595-631.
Mueller-Westerhoff, Ulrich T. et al. "The Synthesis of Dithiolene Dyes with Strong Near-IR Absorption." Tetrahedron. 1991. vol. 47, No. 6, pp. 909-932.
Mueller-Westerhoff, U.T. et al. "Near-IR Dyes for the 1.3 to 1.5 Micron Region: The Use of Substituted Dithiolene Complexes." Mol. Cryst. Leq. Cryst. 1990. vol. 183, pp. 291-302.
Nazzal, Adel and Mueller-Westerhoff, Ulrich T. "Cyclic Electron Delocalization in Transition Metal Complexes with Sulfur-Containing Conjugated Ligands." Transition Met. Chem. 1980. No. 5, pp. 318-320.
Ohki, Akira et al. "Ion Transport Through Liquid Membrane Driven by Redox Potential Multi-Component Ion Carrier as a Mediator." The Chemical Society of Japan: Chemistry Letters.1980. pp. 1591-1594.
Sanders, Richard West Jr. "Synthesis and Inventigation of Square Planar Bis(ferrocenyl) Dithiolene Complexes of Nickel, Palladium, and Platinum: Control of Near-Infrared Absorption and Other Properties by Ligand Modification." Dissertation, University of Connecticut. 2002. pp. 1-119.
Schrauzer, Dr. G.N. et al. "Bis-dithionkemplexe von Ubergangsmetallen." Angew. Chemical. 1964. vol. 76, No. 8, p. 345.
Underhill, A.E. et al. "Developments in the Chemistry of Sulphur-Donor Ligands." Elsevier Science: Synthetic Metals. 1995. vol. 70, pp. 1101-1104.

* cited by examiner

Primary Examiner—Porfirio Nazario-Gonzalez
(74) Attorney, Agent, or Firm—Cantor Colburn LLP

(57) ABSTRACT

Described herein are metal complexes having the formula

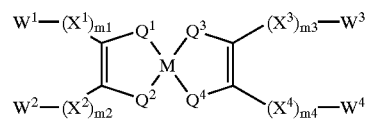

wherein M is nickel, palladium, or platinum; $Q^1$–$Q^4$ are each independently sulfur, selenium, or tellurium; $X^1$–$X^4$ are each independently a divalent linking group having 1 to about 125 carbons; m1 to m4 are each independently 0 or 1; and $W^1$–$W^4$ are each independently hydrogen, carboxylic acid, carboxylic acid anhydride, carboxylic acid chloride, sulfonic acid, or sulfonyl chloride, with the proviso that $W^1$–$W^4$ are not all hydrogen. The complexes have strong absorptions in the near infrared.

29 Claims, No Drawings

FUNCTIONALIZED METAL COMPLEXES

CROSS REFERENCE TO RELATED APPLICATIONS

This application claims priority from Provisional Application Ser. No. 60/378,179, filed May 2, 2002, which is incorporated herein by reference in its entirety.

BACKGROUND

Transition metal dithiolene complexes and their selenium and tellurium analogs have been extensively studied. Reviews of work in this area include, for example, U. T. Mueller-Westerhoff and B. Vance, "Dithiolenes and Related Species", Chapter 16.5 in G. Wilkinson, Ed. "Comprehensive Coordination Chemistry", Pergamon Press, 1987. Some of these complexes are of interest for their oxidation-reduction properties, as well as their ability to efficiently absorb near infrared radiation and thermally dissipate the absorbed energy.

In order to covalently bind a metal dithiolene complex to another molecule, it would be desirable to begin with a metal dithiolene complexes having a reactive functional group. In practice, however, it has been difficult to prepare such complexes because the formation and/or presence of the functional groups has interfered with metal complexation by the dithiolene ligand. There therefore remains a need for functionalized metal dithiolene complexes.

BRIEF SUMMARY

Described herein is a composition comprising a metal complex having the formula (I)

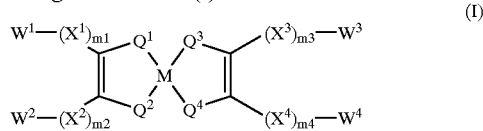

(I)

wherein M is nickel, palladium, or platinum; $Q^1$–$Q^4$ are each independently sulfur, selenium, or tellurium; $X^1$–$X^4$ are each independently a divalent linking group having 1 to about 125 carbons; m1 to m4 are each independently 0 or 1; and $W^1$–$W^4$ are each independently hydrogen, carboxylic acid, carboxylic acid anhydride, carboxylic acid chloride, sulfonic acid, or sulfonyl chloride, with the proviso that $W^1$–$W^4$ are not all hydrogen.

Other embodiments, including functionalized ferrocenyl-substituted metal complexes and functionalized bis-metal complexes, are described below.

DETAILED DESCRIPTION OF THE PREFERRED EMBODIMENTS

One embodiment is a composition comprising a functionalized metal complex having formula (I)

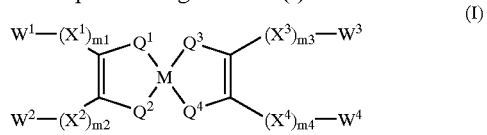

(I)

wherein M is nickel, palladium, or platinum; $Q^1$–$Q^4$ are each independently sulfur, selenium, or tellurium; $X^1$–$X^4$ are each independently a divalent linking group having 1 to about 125 carbons; m1 to m4 are each independently 0 or 1; and $W^1$–$W^4$ are each independently hydrogen, carboxylic acid, carboxylic acid anhydride, carboxylic acid chloride, sulfonic acid, or sulfonyl chloride, with the proviso that $W^1$–$W^4$ are not all hydrogen.

In a preferred embodiment, M is nickel. In another preferred embodiment, $Q^1$–$Q^4$ are sulfur.

Although the metal complexes are herein represented for brevity as having the dithiolene structural unit as follows:

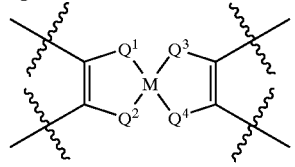

it will be understood that various oxidation states are available to the metal such that the complex can be represented as any one or more of the redox-related complexes as shown below

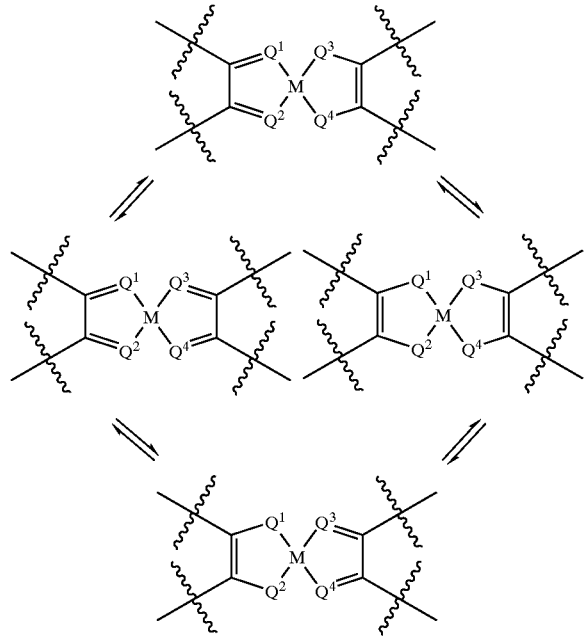

and corresponding to metal oxidation states of 0 to +4. Such structures, and any others that may be present, are within the scope of the dithiolene structure.

In one embodiment, each occurrence of $X^1$–$X^4$ is independently —$(CH_2)_{n1}$— wherein n1 is 1 to 24, —$(V(CH_2)_p)_{n2}$— where V is oxygen or sulfur and p is 2 or 3 and n2 is 1 to 12, —$N(R^2)$—$(CH_2)_{n3}$— where n3 is 1 to 24 and $R^2$ is $C_1$–$C_{12}$ alkyl, —$C(O)(CH_2)_{n4}$— where n4 is 1 to 23, —$C(O)N(R^3)(CH_2)_{n5}$— where n5 is 1 to 23 and $R^3$ is hydrogen or $C_1$–$C_{12}$ alkyl, —$N(R^4)$—$S(O)_2(CH_2)_{n6}$— where n6 is 1 to 24 and $R^4$ is hydrogen or $C_1$–$C_{12}$ alkyl, —$S(CH_2)_{n7}$— where n7 is 1 to 24, —$S(O)(CH_2)_{n8}$— where n8 is 1 to 24, —$S(O)_2$—$(CH_2)_{n9}$— where n9 is 1 to 24, or —$S(O)_2$—$N(R^5)$—$(CH_2)_{n10}$— wherein n10 is 1 to 24 and $R^5$ is hydrogen or $C_1$–$C_{12}$ alkyl. It will be understood that either terminus of a given $X^1$–$X^4$ group above may be attached to the corresponding $W^1$–$W^4$ group, with the other terminus attached to the corresponding dithiolene carbon. For example, when $X^1$ is —$N(R^2)(CH_2)_{n3}$—, it may be attached in the configuration $W^1$—$N(R^2)(CH_2)_{n3}$-(dithiolene)- or in the configuration $W^1$—$(CH_2)_{n3}N(R^2)$-(dithiolene)-.

In a preferred embodiment each occurrence of $W^1$–$W^4$ is independently carboxylic acid (—C(O)OH); carboxylic acid anhydride (—C(O)OC(O)R) wherein R is $C_1$–$C_{12}$ alkyl or $C_6$–$C_{12}$ aryl; or carboxylic acid chloride (—C(O)Cl). In a highly preferred embodiment, each occurrence of $W^1$–$W^4$ is independently carboxylic acid.

In another embodiment, at least one of $X^1$–$X^4$ comprises a ferrocenyl complex. For example, at least one of $X^1$–$X^4$ may have the structure of formula (II)

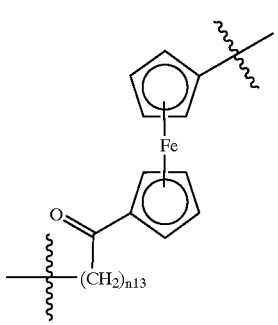

(II)

wherein n13 is 1 to about 12, and the value of the corresponding m1–m4 is one. In other words, $X^1$ has the divalent ferrocenyl structure shown above and m1 is one, and/or $X^2$ has the divalent ferrocenyl structure shown above and m2 is one, and/or $X^3$ has the divalent ferrocenyl structure shown above and m3 is one, and/or $X^4$ has the divalent ferrocenyl structure shown above and m4 is one. In a preferred embodiment, at least two of $X^1$–$X^4$ have the divalent ferrocenyl structure shown above and the values of the corresponding at least two of m1–m4 are one. It will be understood that as used herein, the cyclopentadienyl rings of all ferrocenyl moieties shown and described in this application may include alkyl-substituted analogs, preferably branched or unbranched $C_1$–$C_8$ alkyl-sustituted analogs, including, for example, methycyclopentadienyl, dimethylcyclopentadienyl, trimethylcyclopentadieny, tetramethylcyclopentadienyl, and pentamethylcyclopentadienyl. Varying the degree of alkylation of cyclopentadienyl rings may be used to control the maximum absorption wavelength of the complex.

In another embodiment, the metal complex has one of the structures of Formula (IIIa)–(IIIc):

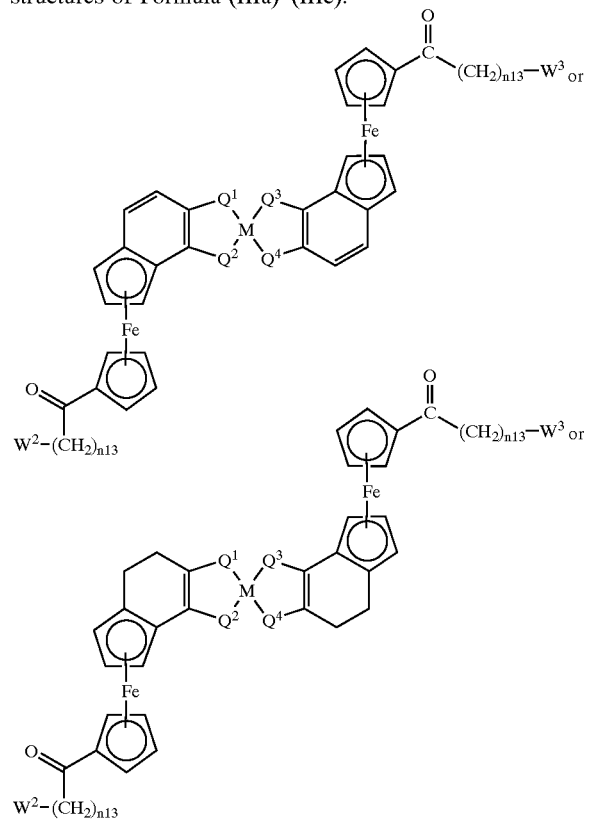

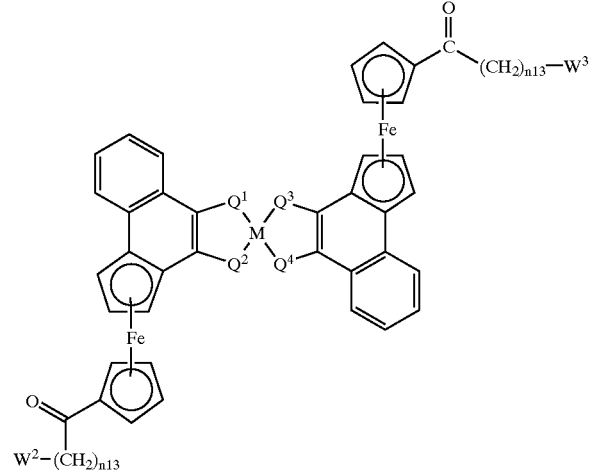

wherein M, $Q^1$–$Q^4$, $W^2$ and $W^3$ are as defined above for formula (I), and n13 is as defined above for Formula (II). Compounds of Formula (III) have the advantage of absorbing strongly in the region of about 1600 to about 1900 nanometers.

Preferably, each occurrence of $W^1$–$W^4$ is independently carboxylic acid (—C(O)OH); carboxylic acid anhydride (—C(O)OC(O)R) wherein R is $C_1$–$C_{12}$ alkyl or $C_6$–$C_{12}$ aryl; or carboxylic acid chloride (—C(O)Cl). In a highly preferred embodiment, each occurrence of $W^1$–$W^4$ is independently carboxylic acid. According, in a preferred embodiment, the functionalized metal complex has formula (IV)

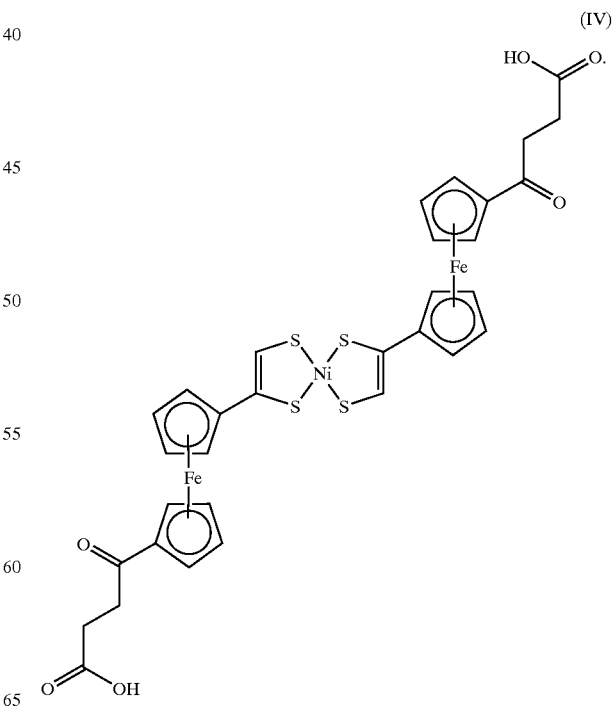

(IV)

Another embodiment is a composition comprising a functionalized metal complex having formula (V)

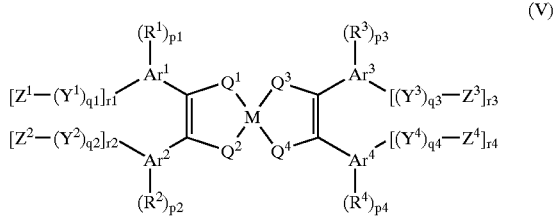

(V)

wherein M is nickel, palladium, or platinum; $Q^1$–$Q^4$ are each independently sulfur, selenium, or tellurium; $Ar^1$–$Ar^4$ are each independently $C_6$–$C_{12}$ arylene, wherein $Ar^1$ and $Ar^2$ may collectively form a $C_2$–$C_{24}$ arylene, and $Ar^3$ and $Ar^4$ may collectively form a $C_{12}$–$C_{24}$ arylene; each occurrence of $R^1$–$R^4$ is independently $C_1$–$C_{12}$ alkyl, $C_1$–$C_{12}$ alkoxy, $C_1$–$C_{12}$ alkylthio, halogen, hydroxy, nitro, cyano, di($C_1$–$C_{12}$)alkylamino, or sulfonamide; each occurrence of p1–p4 is independently 0, 1, 2, 3, 4, or 5; each occurrence of $Y^1$–$Y^4$ is independently a divalent linking group having 1 to about 125 carbons; each occurrence of q1–q4 is independently 0 or 1; each occurrence of $Z^1$–$Z^4$ is independently carboxylic acid, carboxylic acid anhydride, carboxylic acid chloride, sulfonic acid, or sulfonyl chloride; and each occurrence of r1–r4 is independently 0, 1, 2, or 3, with the proviso that at least one of r1–r4 is at least 1.

Referring to formula (V), in a preferred embodiment, M is nickel. In another preferred embodiment, $Q^1$–$Q^4$ are sulfur. In addtion, $Ar^1$–$Ar^4$ are each independently phenylene, diphenylene, naphthylene, or julolidinylene; or $Ar^1$ and $Ar^2$ collectively form a 2,2'-diphenylene and $Ar^3$ and $Ar^4$ collectively form a 2,2'-diphenylene, wherein 2,2'-diphenylene is understood to have the structure

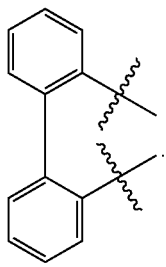

In a preferred embodiment, $Ar^1$–$Ar^4$ are each phenylene.

Referring still to formula (V), in one embodiment at least one of $R^1$–$R^4$ is an electron donating substituent such as di($C_1$–$C_{12}$)alkylamino, and the value of the corresponding at least one p1–p4 is at least 1. It may be preferred that at least two of $R^1$–$R^4$ are electron donating substituents such as di($C_1$–$C_{12}$)alkylamino, and the values of the corresponding at least two of p1 –p4 are at least 1.

In one embodiment, each occurrence of $Y^1$–$Y^4$ is independently —$(CH_2)_{n1}$— wherein n1 is 1 to 24, —$(OCH_2CH_2)_{n2}$— where n2 is 1 to 12, —$N(R^2)(CH_2)_{n3}$— where n3 is 1 to 24 and $R^2$ is $C_1$–$C_{12}$ alkyl, —C(O)$(CH_2)_{n4}$— where n4 is 1 to 23, —C(O)—$N(R^3)$—$(CH_2)_{n5}$— where n5 is 1 to 23 and $R^3$ is hydrogen or $C_1$–$C_{12}$ alkyl, —$N(R^4)S(O)_2(CH_2)_{n6}$— where n6 is 1 to 24 and $R^4$ is hydrogen or $C_1$–$C_{12}$ alkyl, —$S(CH_2)_{n7}$— where n7 is 1 to 24, —$S(O)(CH_2)_{n8}$— where n8 is 1 to 24, —$S(O)_2(CH_2)_{n9}$— where n9 is 1 to 24, or —$S(O)_2$—$N(R^5)(CH_2)_{n10}$— where n10 is 1 to 24 and $R^5$ is hydrogen or $C_1$–$C_{12}$ alkyl. It will be understood that either terminus of a given $Y^1$–$Y^4$ group above may be attached to the corresponding $Z^1$–$Z^4$ group, with the other terminus attached to the corresponding $Ar^1$–$Ar^4$. For example, when $Y^1$ is —$N(R^2)(CH_2)_{n3}$—, it may be attached in the configuration $Z^1$—$N(R^2)(CH_2)_{n3}$—$Ar^1$— or in the configuration $Z^1$—$(CH_2)_{n3}N(R^2)$—$Ar^1$—.

In a preferred embodiment, each occurrence of $Y^1$–$Y^4$ is independently —$(CH_2)_{n1}$— wherein n1 is 1 to 24, or —$N(R^2)(CH_2)_{n3}$— where n3 is 1 to 24 and $R^2$ is hydrogen or $C_1$–$C_{12}$ alkyl.

In another embodiment, at least one of $Y^1$–$Y^4$ comprises a divalent polypeptide, a divalent polysaccharide, or a divalent polynucleotide.

Still referring to formula (V), in a preferred embodiment each occurrence of $Z^1$–$Z^4$ is independently carboxylic acid (—C(O)OH); carboxylic acid anhydride (—C(O)OC(O)R) wherein R is $C_1$–$C_{12}$ alkyl or $C_6$–$C_{12}$ aryl; or carboxylic acid chloride (—C(O)Cl). In a highly preferred embodiment, each occurrence of $W^1$–$W^4$ is independently carboxylic acid.

In another preferred embodiment, at least two of r1–r4 are at least 1.

Another embodiment is a composition comprising a functionalized metal dithiolene complex having formula (VI)

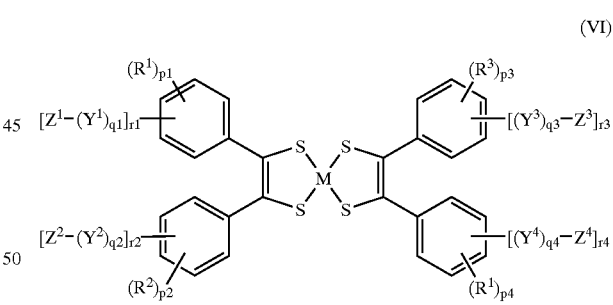

(VI)

wherein M is nickel, palladium, or platinum; each occurrence of $R^1$–$R^4$ is independently $C_1$–$C_{12}$ alkyl, $C_1$–$C_{12}$ alkoxy, $C_1$–$C_{12}$ alkylthio, halogen, hydroxy, nitro, cyano, di($C_1$–$C_{12}$)alkylamino, or sulfonamide; each occurrence of p1–p4 is independently 0, 1, 2, 3, 4, or 5; each occurrence of $Y^1$–$Y^4$ is independently a divalent linking group having 1 to about 125 carbons; each occurrence of q1–q4 is independently 0 or 1; each occurrence of $Z^1$–$Z^4$ is independently carboxylic acid, carboxylic acid anhydride, carboxylic acid chloride, sulfonic acid, or sulfonyl chloride; and each occurrence of r1–r4 is independently 0, 1, 2, or 3, with the proviso that at least one of r1–r4 is at least 1.

In a preferred embodiment, M is nickel.

Another embodiment is a composition comprising a functionalized metal dithiolene complex having formula (VII)

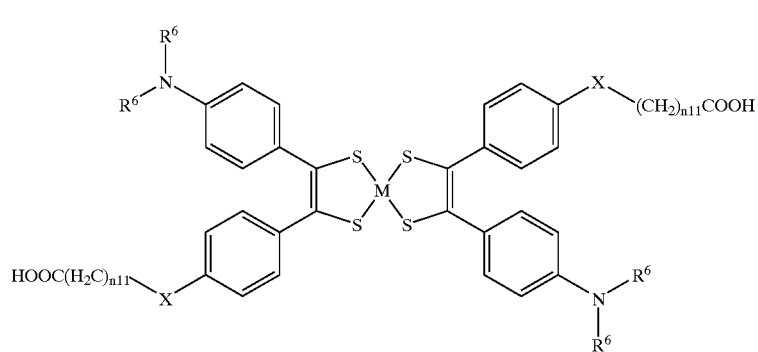

(VII)

wherein M is nickel, palladium, or platinum; each occurrence of $R^6$ is independently $C_1$–$C_{12}$ alkyl; each occurrence of X is independently —$CH_2$— or —C(O); and each occurrence of n11 is independently 1 to 24.

Another embodiment is a composition comprising a functionalized bis-metal dithiolene complex having formula (VIII)

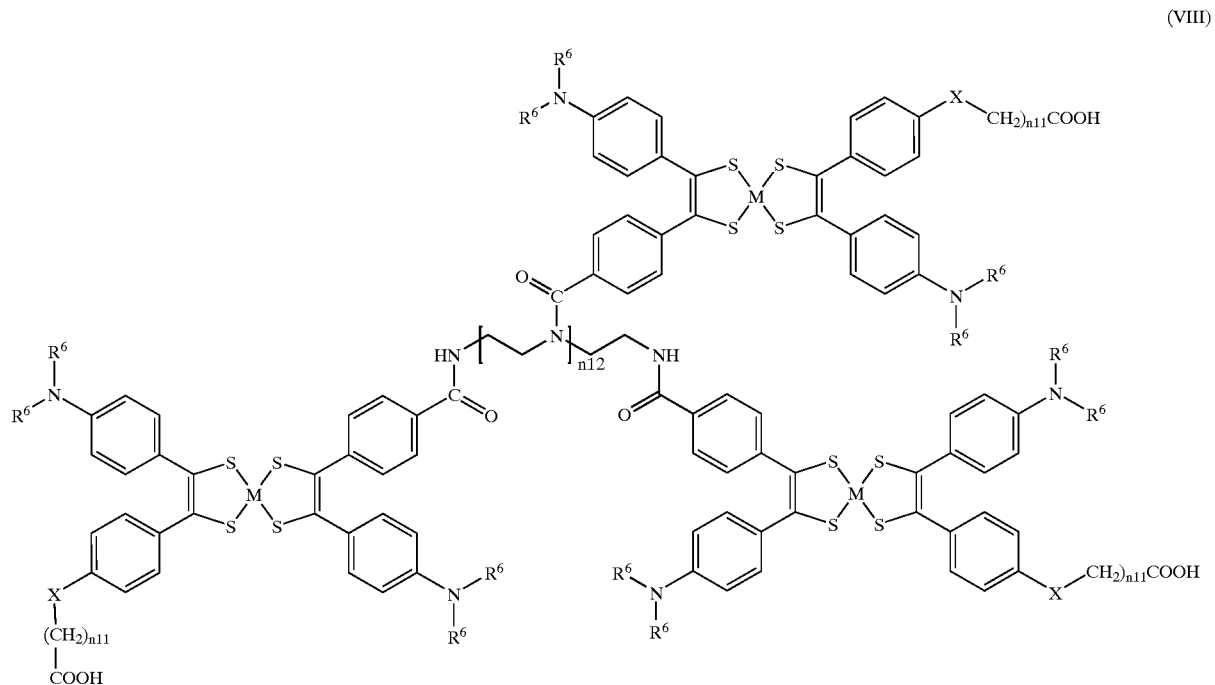

(VIII)

wherein n12 is 0 to about 8, preferably 1 to about 6; and M, $R^6$, X, and n11 are as defined above for formula (VI).

Another embodiment is a composition comprising a functionalized nickel dithiolene complex having formula (IX)

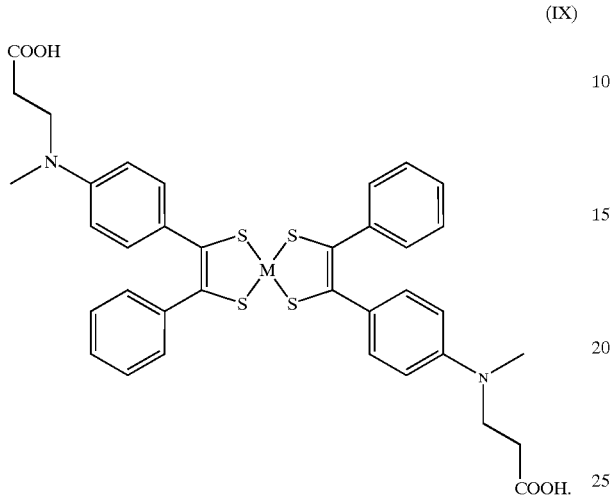

(IX)

Compounds of the generalized formula (VII) can be obtained by first synthesizing the two halves of each ligand, or protected derivatives thereof, in the form of their aldehydes (A) (e.g., A1 and A2, below); then condensing the two halves by one of several methods, such as benzoin condensation or Corey-Seeback umpolung reaction or the like to form B (e.g., B1, below) or one of its derivatives; then converting B to the dithiolene complex VI as described in the literature.

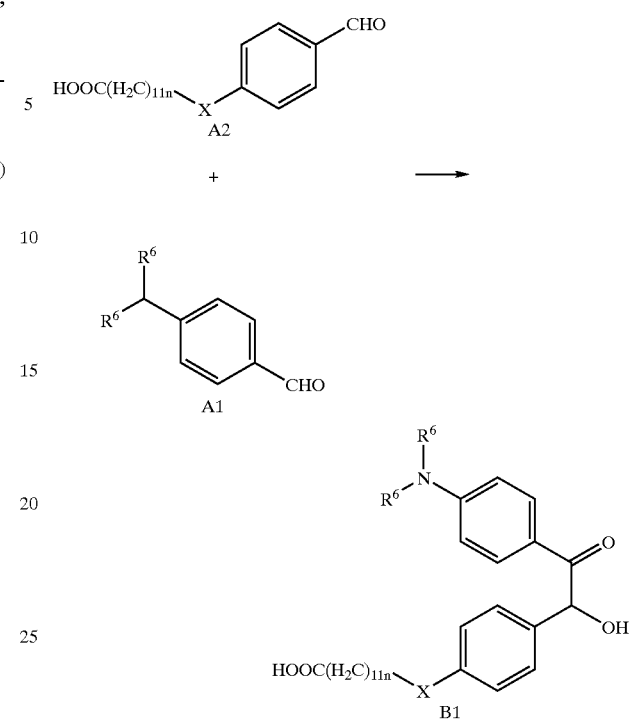

Compounds of the generalized formula (VIII), in which the extinction coefficients are multiplied by attaching several dithiolenes to the same backbone, can be prepared using the syntheses shown below in which (VII) is an intermediate. By reaction with $SOCl_2$ or $(COCl)_2$, (VII) is converted to the acid chloride, which then is added to the polyamine C dissolved in ether or dichloromethane. After addition of an aqueous sodium acetate solution to hydrolyze the unreacted acid chloride functions and acidification to pH 5, the bound dithiolene is isolated and purified.

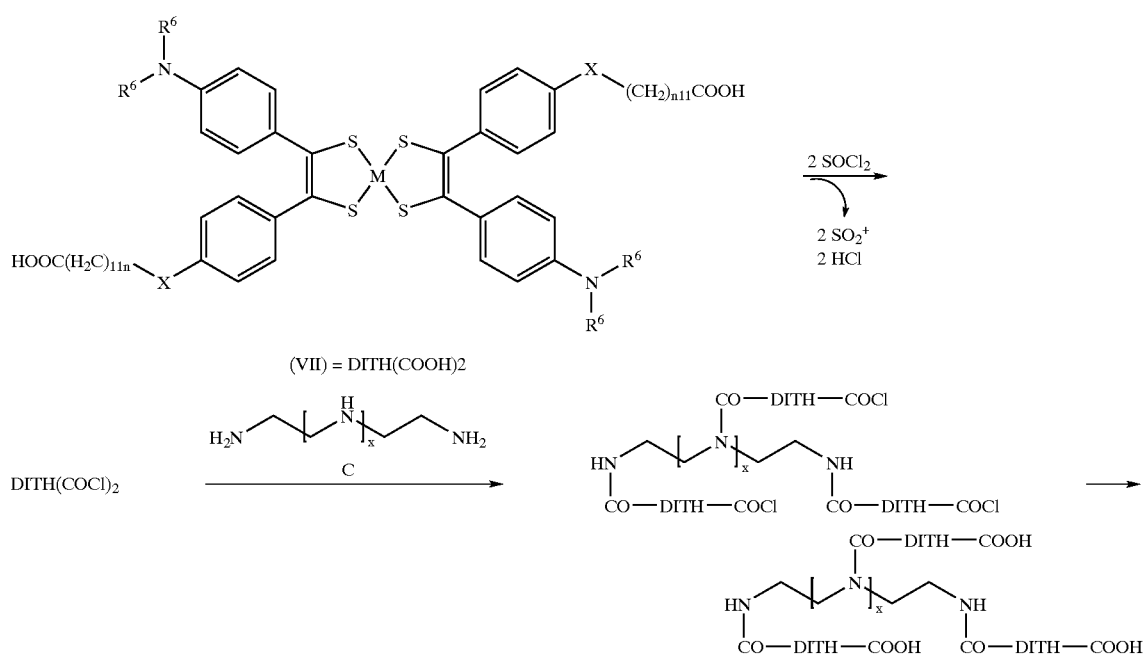

Compounds of structure (IX) may be synthesized by the route shown below. Starting from the commercially available cyano-aldehyde D (Aldrich), a benzoin condensation with benzaldehyde produces the benzoin intermediate E. Refluxing E with phosphorus pentasulfide in dioxane, followed by addition of metal chloride (NiCl$_2$ in the case of (IX), M=Ni) in water and another period of reflux produces the dithiolene F and several byproducts. Separation of F by column chromatography is followed by hydrolysis of the cyano groups through stirring F at room temperature for 24 h in a solution of concentrated HCl in glacial acetic acid to produce (IX).

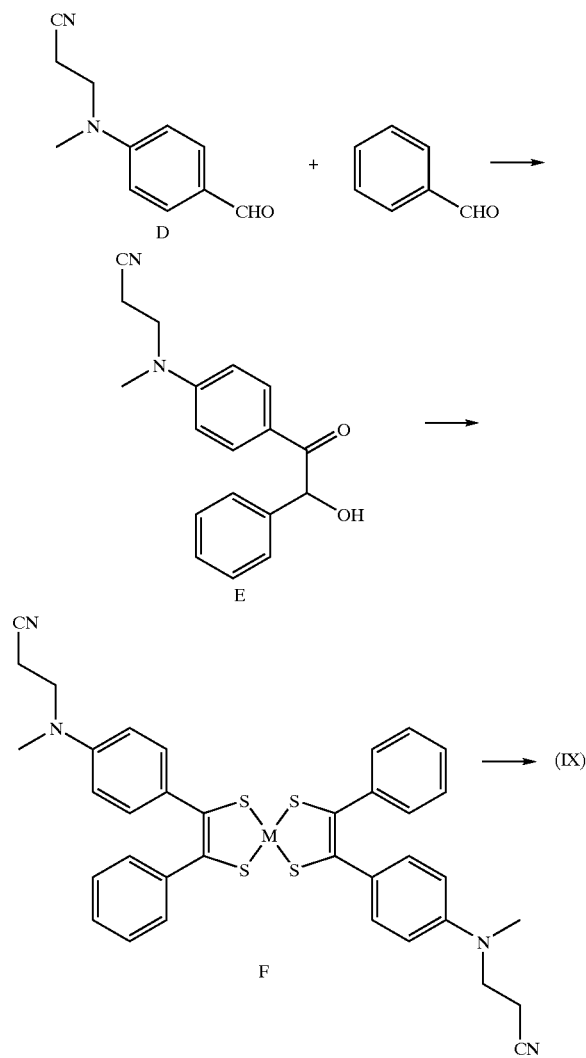

The functionalized metal complex preferably has an extinction coefficient of at least about 10,000 M$^{-1}$cm$^{-1}$ at a wavelength of about 800 to about 2000 nanometers. The extinction coefficient may preferably be at least about 20,000 M$^{-1}$cm$^{-1}$, more preferably at least about 30,000 M$^{-1}$cm$^{-1}$, still more preferably at least about 40,000 M$^{-1}$cm$^{-1}$, yet more preferably at least about 60,000 M$^{-1}$cm$^{-1}$, even more preferably at least about 80,000 M$^{-1}$cm$^{-1}$. In one embodiment, the wavelength may preferably be at least about 900 nm and up to about 1350 nm. In another embodiment, the wavelength may preferably be at least about 1650 nm and up to about 1900 nm.

The functionalized metal complex preferably does not significantly fluoresce or phosphoresce. For example, the functionalized metal complex may have a fluorescence and/or phosphorescence quantum yield of less than or equal to 0.05 for an excitation wavelength of about 800 to about 2000 nanometers. When the metal complex has such low quantum yield for fluorescence and phosphorescence, essentially all absorbed near infrared (NIR) light energy is converted to thermal energy that can be used to heat up the immediate environment of the complex.

The functionalized metal complexes described herein are useful as redox catalysts, as efficient converters of near-infrared radiation to thermal energy, and as conductors of electric current. They may also exhibit unusual magnetic properties. They are also useful as substrates in passive Q-switch and mode-locking applications for different IR lasers (see, for example, U.S. Pat. No. 3,743,964 to Drexhage et al.). They are further useful as redox potential driven electron carriers and cation carriers through artificial membranes (see, for example, J. J. Grimaldi and J. M. Lehn, *J. Am. Chem. Soc.*, 1979, volume 101, pages 1333 ff.; and A. Ohki, M. Takagi, and K. Ueno, *Chem. Lett.*, 1980, pages 1591 ff.).

The invention is further illustrated by the following non-limiting examples.

EXAMPLE 1

This example describes preparation of a functionalized, bis(ferrocenyl)-substituted nickel dithiolene complex. The procedure of Wilkes et al. was used to react α-chloroacetylferrocene (obtained from Aldrich) with ferrocene and aluminum chloride in dichloromethane to produce chloroacetylferrocene. This was reacted with potassium ethylxanthate in ethanol; the product of this reaction was cyclized to form a ferrocenyl dithiocarbonate (4-ferrocenyl-1,3-dithiole-2-one). (See A. E. Underhill, A. Charlton, S. B. Wilkes, I. R. Butler, A. Kobayashi, and H. Kobayashi, *Synth. Met.*, 1995, volume 70, pages 1101 ff.)

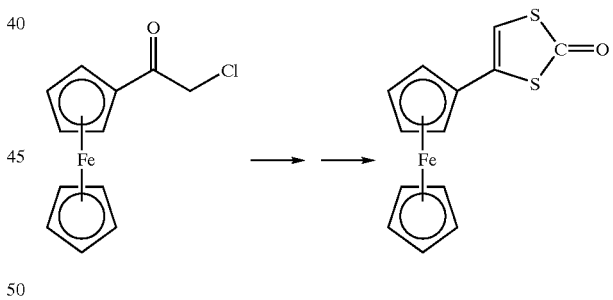

The ferrocenyl dithiocarbonate was reacted with one equivalent of succinic anhydride and three equivalents of aluminum chloride. An 82.7% yield of 4-(1'-succinylferrocenyl)-1,3-dithiole-2-one was obtained following purification by column chromatography.

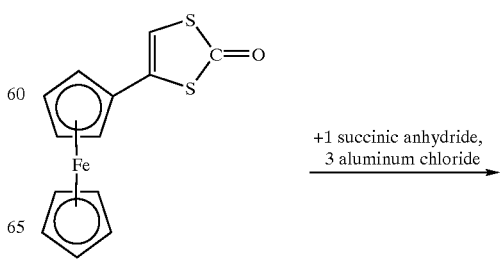

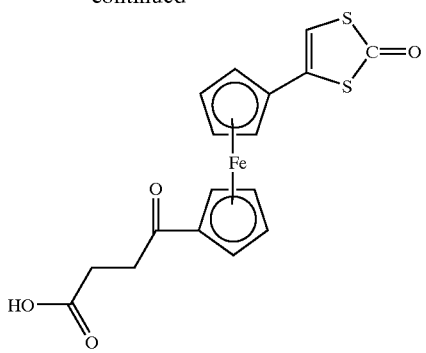

The 6,7-(1'-succinyl)ferrocenyl-3,4-dithiole-2-one was reacted with potassium hydroxide in methanol to form the dithiolate dianion; addition of nickel chloride hexahydrate in methanol/HCl yielded the succinyl-substituted diferrocenyl nickel complex, bis([1'-succinyl ferrocenyl]ethylene-1,2-dithiolato) nickel (II). The product was converted to the neutral nickel (IV) complex by oxidizing with air.

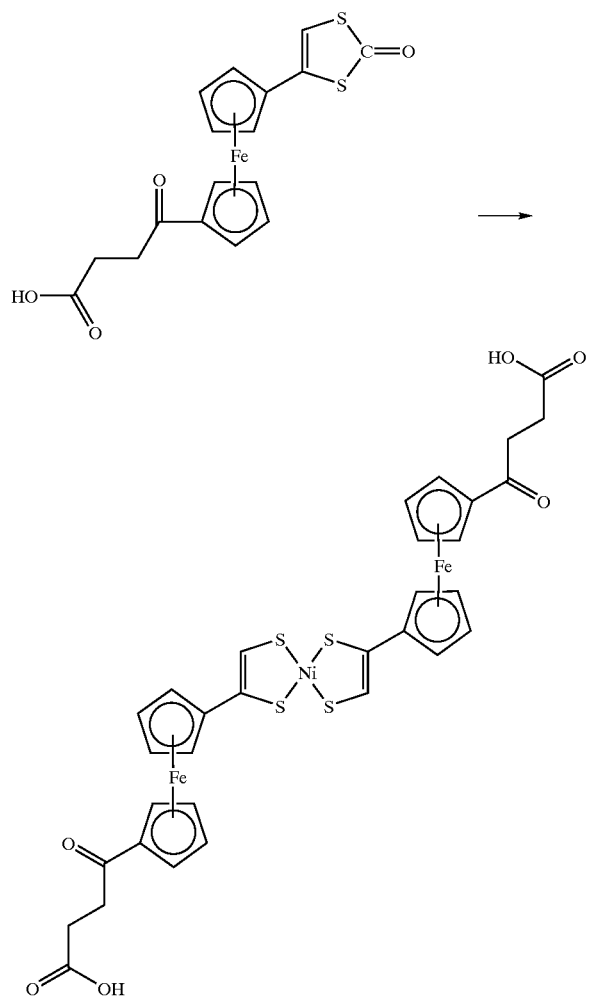

Following oxidation, workup, and isolation of the product mixture, the complex was dissolved in an aqueous 10% KOH solution and filtered. Product was precipitated by acidifying the solution to pH 3, filtered, and washed with water and then hexane to afford the purified complex in 48% yield based on the dithiolene ligand. mp >260° C.; APcI$^-$ MS m/e 805.7 (M$^-$, calc. 805.88); Near IR $\lambda_{1max}/\lambda_{2max}$ (CH$_2$Cl$_2$) 1106 nm (broad, strong)/735 nm, (DMF) 1140 nm (broad, strong)/752 nm, (DMF) 1007 nm (monoanionic species, (H$_2$O, pH 3) 1180 nm (broad, strong)/748 nm, (H$_2$O, pH 7.5) 1068 nm, (H$_2$O, pH 9) 163 nm.

EXAMPLE 2

This example summarized procedures used in multiple preparations of a functionalized bis(dialkylamino)-substituted nickel dithiolene complex. The commercially available (Aldrich) material 4-(2-cyanoethyl-methylamino) benzaldehyde was subjected to a benzoin condensation with benzaldehyde (NaCN catalyst in either ethanol/water or N,N-dimethylformamide/water at temperatures varying between 20° C. and the boiling point of the reaction mixture) to produce a mixture of products, of which the desired benzoin was a more or less abundant part. Optimization of the reaction conditions allowed the synthesis of the benzoin as the major product. The purification involved repeated column chromatography and recrystallizations for an overall yield of pure benzoin varying between 25 and 60%. In this manner, sufficient quantities of the benzoin were obtained to proceed to the next step.

The benzoin was treated with P$_4$S$_{10}$ in dioxane (reflux, 2 h) and the mixture was reacted at reflux with NiCl$_2$·6H$_2$O in water containing HCl to produce the dithiolene complex carrying two cyano functionalities. This complex was purified by column chromatography.

In the final step, the dicyano derivative was hydrolyzed (anhydrous HCl/acetic acid, room temperature, 2 days) to produce the desired diacid.

The product was recrystallized from ethyl acetate and characterized by Vis-NIR spectroscopy ($\lambda_{max}$=1058 nm) and APcI mass spectrometry. The success of this synthetic approach was not necessarily expected because the cyano group could have interfered in the sulfurization reaction, and the final hydrolysis could have destroyed the dithiolene complex.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

What is claimed is:

1. A composition comprising a metal complex having the formula

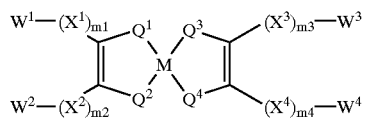

wherein
M is nickel, palladium, or platinum;
$Q^1$–$Q^4$ are each independently sulfur, selenium, or tellurium;
$X^1$–$X^4$ are each independently a divalent linking group having 1 to about 125 carbons;
m1 to m4 are each independently 0 or 1; and
$W^1$–$W^4$ are each independently hydrogen, carboxylic acid, carboxylic acid anhydride, carboxylic acid chloride, sulfonic acid, or sulfonyl chloride, with the proviso that $W^1$–$W^4$ are not all hydrogen.

2. The composition of claim 1, wherein M is nickel.

3. The composition of claim 1, wherein $Q^1$–$Q^4$ are sulfur.

4. The composition of claim 1, wherein each $X^1$–$X^4$ is independently —$(CH_2)_{n1}$— wherein n1 is 1 to 24, —$(V(CH_2)_p)_{n2}$— where V is oxygen or sulfur and p is 2 or 3 and n2 is 1 to 12, —$N(R^2)(CH_2)_{n3}$— where n3 is 1 to 24 and $R^2$ is $C_1$–$C_{12}$ alkyl, —$C(O)(CH_2)_{n4}$— where n4 is 1 to 23, —$C(O)N(R^3)(CH_2)_{n5}$— where n5 is 1 to 23 and $R^3$ is hydrogen or $C_1$–$C_{12}$ alkyl, —$N(R^4)S(O)_2(CH_2)_{n6}$— where n6 is 1 to 24 and $R^4$ is hydrogen or $C_1$–$C_{12}$ alkyl, —$S(CH_2)_{n7}$— where n7 is 1 to 24, —$S(O)(CH_2)_{n8}$— where n8 is 1 to 24, —$S(O)_2(CH_2)_{n9}$— where n9 is 1 to 24, or —$S(O)_2N(R^5)(CH_2)_{n10}$— where n10 is 1 to 24 and $R^5$ is hydrogen or $C_1$–$C_{12}$ alkyl.

5. The composition of claim 1, wherein at least one of $X^1$–$X^4$ is

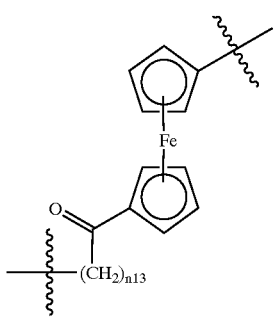

wherein n13 is 1 to about 12, and the value of the corresponding m1–m4 is one.

6. The composition of claim 1, wherein each occurrence of $W^1$–$W^4$ is independently a carboxylic acid, a carboxylic acid anhydride of the formula —C(O)OC(O)R wherein R is $C_1$–$C_{12}$ alkyl or $C_{6-12}$ aryl, or a carboxylic acid chloride.

7. The composition of claim 1, wherein each occurrence of $W^1$–$W^4$ is carboxylic acid.

8. The composition of claim 1, wherein the metal complex has an extinction coefficient of at least about 10,000 $M^{-1}cm^{-1}$ at a wavelength of about 800 to about 2000 nanometers.

9. The composition of claim 1, wherein the metal complex has an extinction coefficient of at least about 20,000 $M^{-1}cm^{-1}$ at a wavelength of about 900 to about 1350 nanometers.

10. The composition of claim 1, wherein the metal complex has an extinction coefficient of at least about 20,000 $M^{-1}cm^{-1}$ at a wavelength of about 1650 to about 1900 nanometers.

11. The composition of claim 1, wherein the metal complex has a fluorescence and/or phosphorescence quantum yield of less than or equal to 0.05 for an excitation wavelength of about 800 to about 2000 nanometers.

12. A composition comprising a metal complex having the formula

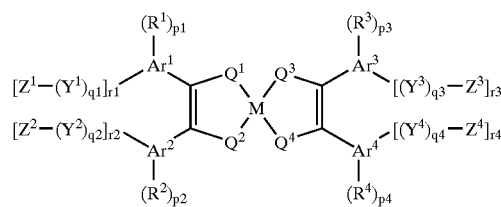

wherein
M is nickel, palladium, or platinum;
$Q^1$–$Q^4$ are each independently sulfur, selenium, or tellurium;
$Ar^1$–$Ar^4$ are each independently $C_6$–$C_{12}$ arylene, wherein $Ar^1$ and $Ar^2$ may collectively form a $C_{12}$–$C_{24}$ arylene, and $Ar^3$ and $Ar^4$ may collectively form a $C_{12}$–$C_{24}$ arylene;
each occurrence of $R^1$–$R^4$ is independently $C_1$–$C_{12}$ alkyl, $C_1$–$C_{12}$ alkoxy, $C_1$–$C_{12}$ alkylthio, halogen, hydroxy, nitro, cyano, di($C_1$–$C_{12}$)alkylamino, or sulfonamide;
each occurrence of p1–p4 is independently 0, 1, 2, 3, 4, or 5;
each occurrence of $Y^1$–$Y^4$ is independently a divalent linking group having 1 to about 125 carbons;
each occurrence of q1–q4 is independently 0 or 1;
each occurrence of $Z^1$–$Z^4$ is independently carboxylic acid, carboxylic acid anhydride, carboxylic acid chloride, sulfonic acid, or sulfonyl chloride; and
each occurrence of r1–r4 is independently 0, 1, 2, or 3, with the proviso that at least one of r1–r4 is at least 1.

13. The composition of claim 12, wherein M is nickel.

14. The composition of claim 12, wherein $Q^1$–$Q^4$ are sulfur.

15. The composition of claim 12, wherein $Ar^1$–$Ar^4$ are each independently phenylene, diphenylene, naphthylene, or julolidinylene; or $Ar^1$ and $Ar^2$ collectively form a 2,2'-diphenylene and $Ar^3$ and $Ar^4$ collectively form a 2,2'-diphenylene.

16. The composition of claim 12, wherein $Ar^1$–$Ar^4$ are each phenylene.

17. The composition of claim 12, wherein at least one of $R^1$–$R^4$ is di($C_1$–$C_{12}$)alkylamino and the value of the corresponding p1–p4 is at least 1.

18. The composition of claim 12, wherein each occurrence of $Y^1$–$Y^4$ is independently —$(CH_2)_{n1}$— wherein n1 is 1 to 24, —$(OCH_2CH_2)_{n2}$— where n2 is 1 to 12, —$N(R^2)(CH_2)_{n3}$— where n3 is 1 to 24 and $R^2$ is $C_1$–$C_{12}$ alkyl, —$C(O)(CH_2)_{n4}$— where n4 is 1 to 23, —$C(O)N(R^3)(CH_2)_{n5}$— where n5 is 1 to 23 and $R^3$ is hydrogen or $C_1$–$C_{12}$ alkyl, —$N(R^4)S(O)_2(CH_2)_{n6}$— where n6 is 1 to 24 and $R^4$ is hydrogen or $C_1$–$C_{12}$ alkyl, —$S(CH_2)_{n7}$— where n7 is 1 to 24, —$S(O)(CH_2)_{n8}$— where n8 is 1 to 24, —$S(O)_2$ $(CH_2)_{n9}$— where n9 is 1 to 24, or —$S(O)_2N(R^5)(CH_2)_{n10}$— where n10 is 1 to 24 and $R^5$ is hydrogen or $C_1$-$C_{12}$ alkyl.

19. The composition of claim 12, wherein each occurrence of $Y^1$-$Y^4$ is independently —$(CH_2)_{n1}$— wherein n1 is 1 to 24, or —$N(R^2)(CH_2)_{n3}$— where n3 is 1 to 24 and $R^2$ is hydrogen or $C_1$-$C_{12}$ alkyl.

20. The composition of claim 12, wherein one to three of $Y^1$-$Y^4$ comprises a divalent polypeptide, a divalent polysaccharide, or a divalent polynucleotide.

21. The composition of claim 12, wherein each occurrence of $Z^1$-$Z^4$ is independently a carboxylic acid, a carboxylic acid anhydride of the formula —C(O)OC(O)R wherein R is $C_1$-$C_{12}$ alkyl or $C_6$-$C_{12}$ aryl, or a carboxylic acid chloride.

22. The composition of claim 11, wherein each occurrence of $Z^1$-$Z^4$ is carboxylic acid.

23. The composition of claim 11, wherein at least two of r1–r4 are at least 1.

24. A composition comprising a metal complex having the formula

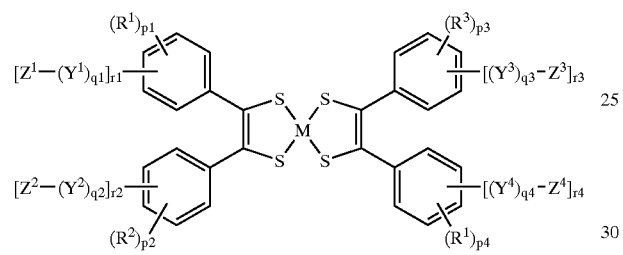

wherein
M is nickel, palladium, or platinum;
each occurrence of $R^1$-$R^4$ is independently $C_1$-$C_{12}$ alkyl, $C_1$-$C_{12}$ alkoxy, $C_1$-$C_{12}$ alkylthio, halogen, hydroxy, nitro, cyano, di($C_1$-$C_{12}$)alkylamino, or sulfonamide;
each occurrence of p1–p4 is independently 0, 1, 2, 3, 4, or 5;
each occurrence of $Y^1$-$Y^4$ is independently a divalent linking group having 1 to about 125 carbons;
each occurrence of q1–q4 is independently 0 or 1;
each occurrence of $Z^1$-$Z^4$ is independently carboxylic acid, carboxylic acid anhydride, carboxylic acid chloride, sulfonic acid, or sulfonyl chloride; and
each occurrence of r1–r4 is independently 0, 1, 2, or 3, with the proviso that at least one of r1–r4 is at least 1.

25. The composition of claim 24, wherein M is nickel.

26. The composition of claim 24, having the formula

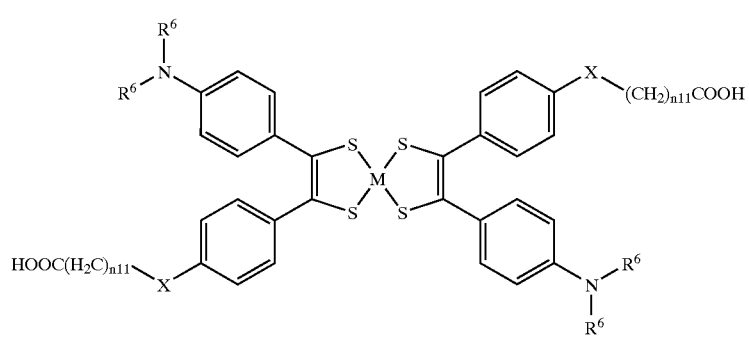

wherein M is nickel, palladium, or platinum; each occurrence of $R^6$ is independently $C_1$-$C_{12}$ alkyl; each occurrence of X is independently —$CH_2$— or —C(O)—; and each occurrence of n11 is independently 1 to 24.

27. The composition of claim 26, comprising a nickel dithiolene complex having the formula

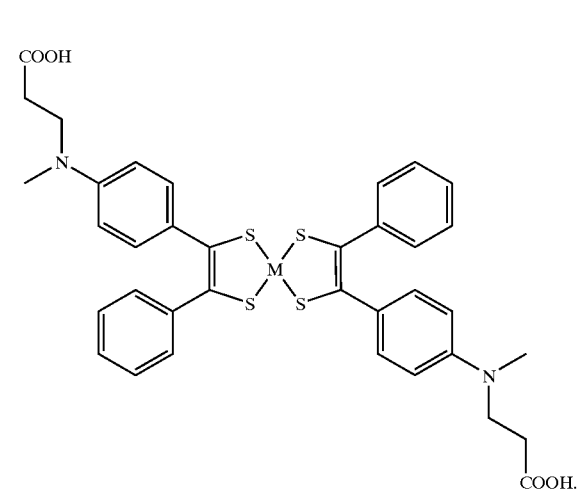

28. A composition comprising a metal dithiolene complex having the formula

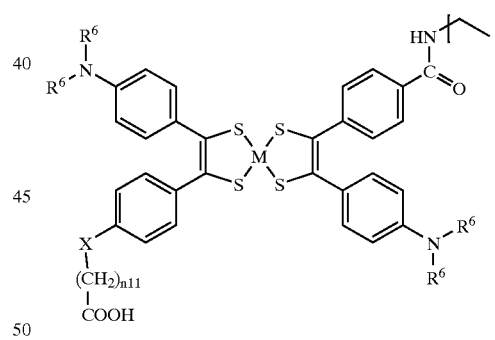

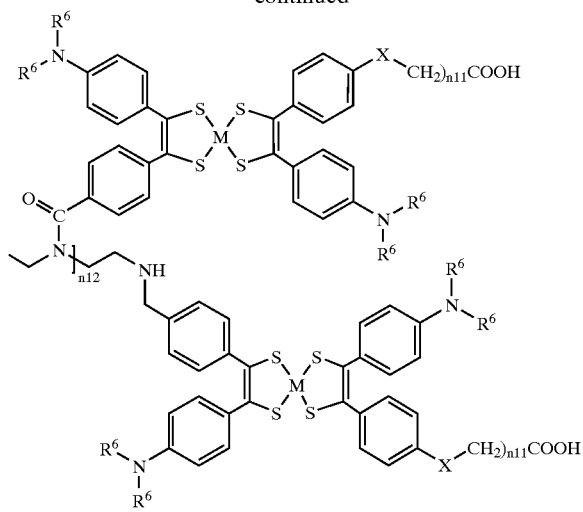

wherein M is nickel, palladium, or platinum; each occurrence of $R^6$ is independently $C_1$–$C_{12}$ alkyl; each occurrence of X is independently —$CH_2$— or —C(O)—; each occurrence of n11 is independently 1 to 24; and n12 is 0 to 8.

29. The composition of claim 1 comprising a nickel dithiolene complex having the formula

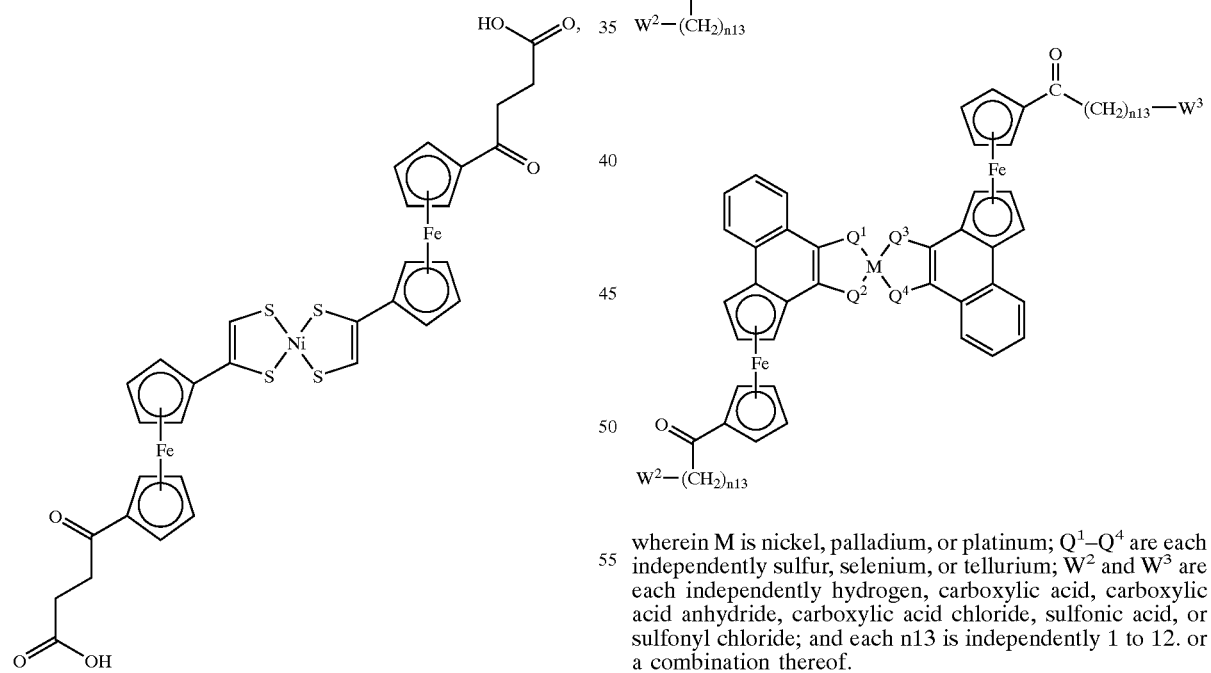

wherein M is nickel, palladium, or platinum; $Q^1$–$Q^4$ are each independently sulfur, selenium, or tellurium; $W^2$ and $W^3$ are each independently hydrogen, carboxylic acid, carboxylic acid anhydride, carboxylic acid chloride, sulfonic acid, or sulfonyl chloride; and each n13 is independently 1 to 12. or a combination thereof.

* * * * *